(12) United States Patent
Kim

(10) Patent No.: US 9,957,545 B2
(45) Date of Patent: May 1, 2018

(54) BLOOD GLUCOSE MEASUREMENT UNIT, BLOOD GLUCOSE MEASUREMENT SYSTEM COMPRISING SAME

(75) Inventor: Sanghyo Kim, Yongin-si (KR)

(73) Assignee: GACHON UNIVERSOTY OF INSUTRY—ACADEMIC COOPERATION FOUNDATION, Seongnam-si (KR)

( * ) Notice: Subject to any disclaimer, the term of this patent is extended or adjusted under 35 U.S.C. 154(b) by 0 days. days.

(21) Appl. No.: 14/371,629

(22) PCT Filed: Jan. 11, 2012

(86) PCT No.: PCT/KR2012/000247
§ 371 (c)(1),
(2), (4) Date: Jul. 10, 2014

(87) PCT Pub. No.: WO2013/105678
PCT Pub. Date: Jul. 18, 2013

(65) Prior Publication Data
US 2014/0377788 A1    Dec. 25, 2014

(51) Int. Cl.
*C12Q 1/54* (2006.01)
*G01N 33/52* (2006.01)
(Continued)

(52) U.S. Cl.
CPC ............... *C12Q 1/54* (2013.01); *C12Q 1/26* (2013.01); *G01N 33/52* (2013.01); *G01N 33/558* (2013.01);
(Continued)

(58) Field of Classification Search
None
See application file for complete search history.

(56) References Cited

U.S. PATENT DOCUMENTS 5,948,695 A * 9/1999 Douglas ............... B01L 3/5023
422/401
6,518,034 B1 2/2003 Phillips et al.
(Continued)

FOREIGN PATENT DOCUMENTS

| EP | 1 860 443 A1 | 11/2007 |
| KR | 10-2006-0133989 A | 12/2006 |
| KR | 10-2007-0006304 A | 1/2007 |

OTHER PUBLICATIONS

International Search Report for Application No. PCT/KR2012/000247 dated Sep. 27, 2012.

*Primary Examiner* — Samuel P Siefke
(74) *Attorney, Agent, or Firm* — STIP Law Group, LLC

(57) ABSTRACT

A blood glucose measurement unit, a blood glucose measurement method, and a blood glucose measurement system comprising the same are disclosed. According to one aspect of the present invention, provided is a blood glucose measurement unit comprising: a transparent first substrate consisting of a blood inflow region into which blood flows and a reaction region connected to the blood inflow region which are formed on one surface thereof; a transparent second substrate coupled to the first substrate and comprising a blood aperture through which the blood flowing into the blood inflow region passes; and a reagent distributed to the reaction region so as to react with the blood glucose of the blood which has flown into the blood inflow region.

10 Claims, 3 Drawing Sheets

(51) Int. Cl.
    *G01N 33/66*     (2006.01)
    *G01N 33/558*     (2006.01)
    *C12Q 1/26*     (2006.01)

(52) U.S. Cl.
    CPC ......... *G01N 33/66* (2013.01); *G01N 2400/00* (2013.01); *G01N 2800/042* (2013.01)

(56) References Cited

U.S. PATENT DOCUMENTS

| | | |
|---|---|---|
| 8,001,857 B2 | 8/2011 | Kahl |
| 2014/0158553 A1 | 6/2014 | Fujiwara et al. |

\* cited by examiner

BLOOD GLUCOSE MEASUREMENT UNIT, BLOOD GLUCOSE MEASUREMENT SYSTEM COMPRISING SAME

CROSS-REFERENCE TO RELATED APPLICATIONS

This application is a national stage application filed under 35 U.S.C. 371 of International Application No. PCT/KR2012/000247, entitled "Blood Glucose Measurement Unit, Blood Glucose Measurement System Comprising Same, and Blood Glucose Measurement Method," filed Jan. 11, 2012, the contents of which are incorporated herein in their entirety.

TECHNICAL FIELD

The present invention relates, in general, to a unit for measuring the level of blood glucose, a system containing the same and a method for measuring the level of blood glucose.

BACKGROUND ART

Recently, with a growing number of patients suffering from diabetes, a representative adult disease, there have been increasing demands for a technology for measuring the blood glucose level of diabetes patients.

However, the conventional devices for measuring glucose levels in blood employ a biological enzymatic method, requiring a routine exchange of an enzyme sensor once every two to three days. Additionally, the conventional glucose level measuring device had too complicated a structure to economically and easily manufacture and was not easily transportable due to its large volume.

Accordingly, there is an urgent need for the development of a technology for measuring blood glucose level with improved user convenience in a real-life usage environment, while still providing accurate and trustworthy real-time data on a user's blood glucose level.

DISCLOSURE

Technical Problem

Accordingly, the present invention has been made keeping in mind the above problems occurring in the prior art, and the objects of the present invention are to provide a unit for measuring blood glucose level with simple features capable of measuring real-time blood glucose level, a method for measuring the blood glucose level, and a system including the same.

Technical Solution

In order to accomplish the above objects, the present invention provides a blood glucose measurement unit including: a transparent first substrate, including a blood inflow region into which blood flows and a reaction region connected to the blood inflow region, which are formed on one surface thereof; a transparent second substrate coupled to the first substrate and including a blood aperture through which the blood flowing into the blood inflow region passes; and a reagent distributed to the reaction region so as to react with the glucose in the blood which has flown into the blood inflow region.

The reagent may include at least one selected from the group consisting of: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase.

Additionally, in the reagent, the weight ratio between at least one selected from the group consisting of: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase may be in the range of from 0.01 to 40, preferably from 0.05 to 5, and more preferably from 0.1 to 2.

Additionally, the reagent may further contain a peroxidase. The weight ratio of peroxidase relative to glucose oxidase may be in the range of from 0.01 to 10, preferably from 0.05 to 5, and more preferably from 0.1 to 1.

The blood glucose measurement unit may further include a transparent third substrate to be inserted between the first substrate and the second substrate, and a blood aperture, through which the blood flowing into the blood inflow region passes, may be formed on the third substrate.

The blood glucose measurement unit may further include a filter to be in between the first substrate and the second substrate so as to separate proteins and blood corpuscles out of the blood which passes through the blood aperture.

The filter may contain at least one selected from the group consisting of: nitrocellulose, polysulfone and nonwoven fiber.

A projection surrounding the blood inflow region may be formed on one surface of the first substrate, and an opening may be formed on the projection so that the blood in the blood inflow region may move to the reaction region.

An aperture may be formed in a position of the second substrate corresponding to an end of the reaction region.

The first substrate and the second substrate may respectively include at least one selected from the group consisting of: polyester, polyacrylate, polyethylene (PE), polyethersulfone (PES), polycarbonate (PC), polyarylate (PAR), polyimide (PI) and glass.

The polyester may be at least one selected from the group consisting of (PET) and polyethylene naphthalate (PEN).

According to another aspect of the present invention, there is provided a blood glucose measurement system including the blood glucose measurement unit described above; and a CMOS image sensor for counting the number of photons that penetrate the blood glucose measurement unit.

The CMOS image sensor may be installed on at least one selected from the group consisting of smart phones and cameras.

In particular, the at least one selected from the group consisting of smart phones and cameras may be provided with a built-in application capable of quantitatively expressing the number of photons counted by the CMOS image sensor.

According to a further aspect of the present invention, there is provided a blood glucose measurement method, including: counting the number of photons that penetrate the blood glucose measurement unit in advance using a CMOS image sensor; injecting a blood sample into the blood glucose measurement unit; reacting the blood sample injected into the blood glucose measurement unit with a reagent contained in the blood glucose measurement unit; and recounting the number of photons that penetrate the blood glucose measurement unit using the CMOS image sensor.

Advantageous Effects

According to an embodiment of the present invention, a real-time measurement of blood glucose can be performed with convenience and effectiveness using an easily portable blood glucose measurement unit and a CMOS image sensor.

In particular, the portability of the glucose measurement unit can be maximized by installing the CMOS image sensor on a smart phone, etc.

MODE FOR INVENTION

Figure 1:
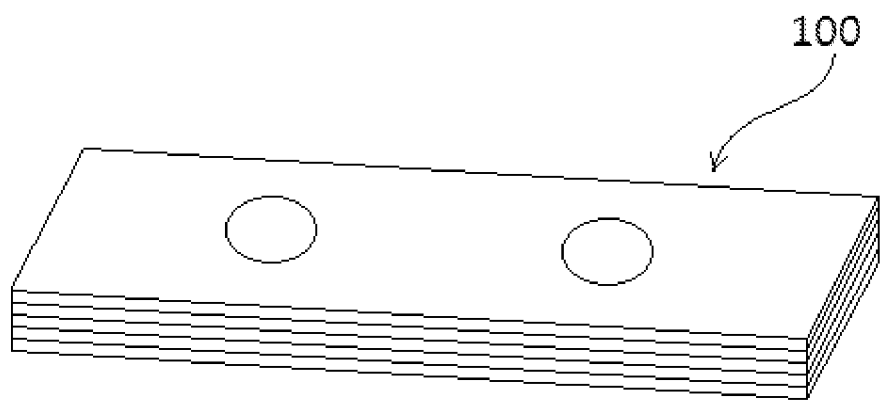
FIG. 1 is a schematic diagram illustrating a blood glucose measurement system according to an embodiment of the present invention.
Figure 1:
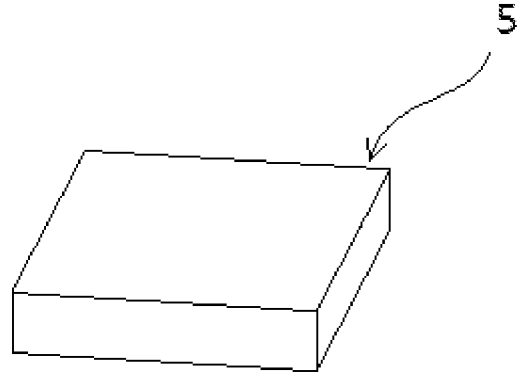

While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims. However, in the following description of the invention, if the related known functions or specific instructions on configuring the present invention unnecessarily obscure the gist of the invention, the detailed description thereof will be omitted.

It will be understood that, although the terms "first," "second," etc., may be used herein to describe various elements, these elements should not be limited by these terms. These terms are only used to distinguish one element from another element.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Herein below, exemplary embodiments of the present invention will be described in detail with reference to the accompanying drawings. Throughout the drawings, the same reference numerals will refer to the same or like parts, and any repeated explanations thereof will be omitted.

Figure 2:
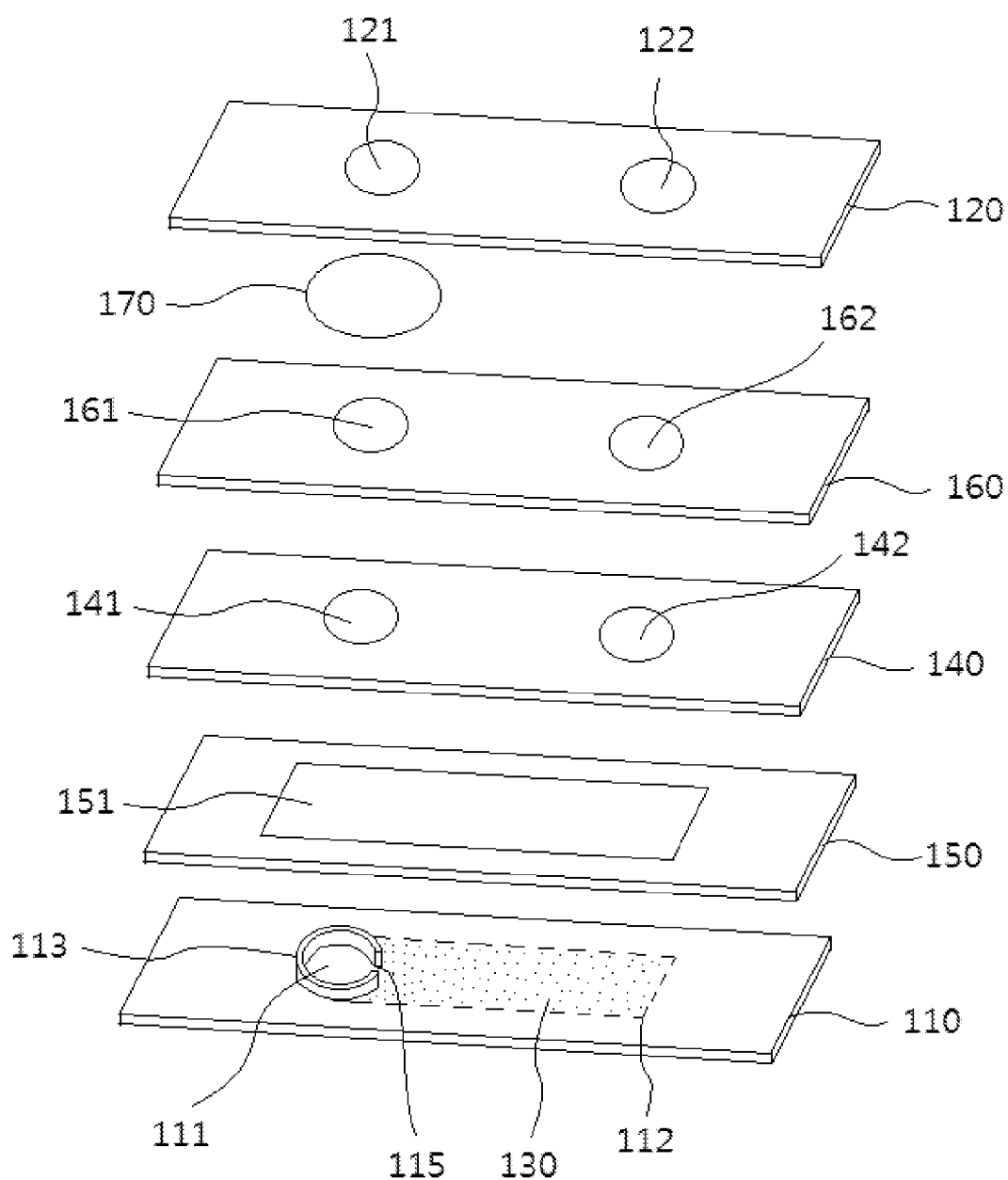
FIG. 2 is an exploded perspective view of a blood glucose measurement unit included in the blood glucose measurement system according to an embodiment of the present invention.

FIG. 1 is a schematic diagram illustrating a blood glucose measurement system according to an embodiment of the present invention, and FIG. 2 is an exploded perspective view of a blood glucose measurement unit included in the blood glucose measurement system according to an embodiment of the present invention.

First, referring to FIG. 1, a blood glucose measurement system 1 according to the present invention may include a blood glucose measurement unit 100 and a CMOS image sensor 5.

According to an embodiment of the present invention, a blood glucose level may be effectively and promptly obtained by measuring the level of light transmittance relative to the blood glucose measurement unit 100 using the CMOS image sensor 5, in particular, the CMOS image sensor 5 installed on a smart phone or a camera.

Referring to FIG. 2, the blood glucose measurement unit 100 according to an embodiment of the present invention may include a first substrate 110 a second substrate 120, and a reagent 130.

The first substrate 110 has a light transmittance. The first substrate 110 may contain at least one selected from the group consisting of: polyester, polyacrylate, polyethylene (PE), polyethersulfone (PES), polycarbonate (PC), polyarylate (PAR), polyimide (PI) and glass, but is not limited thereto.

For example, when the first substrate 110 is manufactured using polyester it may have a shape of a thin film such as an overhead projector (OHP) film. The blood glucose measurement unit 100 manufactured as such will have an improved flexibility thus being convenient to transport.

On one surface of the first substrate 110 is formed a blood inflow region 111. The blood sample to measure will be flowed into the blood inflow region 111 on the first substrate 110. In particular, a projection 113 surrounding the blood inflow region 111 may be formed on one surface of the first substrate 110. As such, the blood entered into the blood inflow region 111 can be prevented from being flowed out thereby enabling an effective measurement of blood glucose level.

When the projection 113 is formed on one surface of the first substrate 110, an opening 115 may be formed on the projection 113 so that the blood in the blood inflow region 111 may move to a reaction region 112 described below.

On one surface of the first substrate 110 is formed the reaction region 112 connected to the blood inflow region 111. As shown in FIG. 2, the reaction region 112 may be formed extendedly toward a direction departing from the blood inflow region 111 while being connected to the blood inflow region 111, but is not limited thereto. A reagent 130, described below, is distributed on the reaction region 112.

The second substrate 120 is connected to the first substrate 110. The first substrate 110 and the second substrate 120 may be mutually connected by an adhesive. In this regard, FIG. 2 shows that two adhesive layers 150 and 160 formed in between the first substrate 110 and the second substrate 120, however, FIG. 2 is in fact provided to explain the embodiment of the present invention, in which a third substrate 140 is further included thereinbetween. Accordingly, when the third substrate 140 is excluded, a single adhesive layer may be applied in between the first substrate 110 and the second substrate 120.

The second substrate 120 has a light transmittance. The second substrate 120 may contain polyester, polyacrylate, polyethylene (PE), polyethersulfone (PES), polycarbonate (PC), polyarylate (PAR), polyimide (PI) or glass, but is not limited thereto.

For example, when the second substrate 120 is manufactured using polyester it may have a shape of a thin film such as an overhead projector (OHP) film. The blood glucose measurement unit 100 manufactured as such will have an improved flexibility thus being convenient to transport.

On the second substrate 120 is formed a blood aperture 121. The blood sample to measure will be flowed into the blood inflow region 111 on the first substrate 110 through the blood aperture 121 formed on the second substrate 120. In particular, the blood aperture 121 may be formed in a position corresponding to the blood inflow region 111.

A reagent 130 is distributed on the reaction region 112 of the first substrate 110. The reagent 130 reacts with glucose in blood. The blood entered into the blood inflow region 111 may be transported into the reaction region 112, for example, by gravity, and the blood transported to the reaction region 112 will react with the reagent 130.

The reagent 130 may include at least one selected from: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase.

The reactions between O-dianisidine, as a reagent 130, and glucose oxidase and blood glucose are proceeded with as shown below in Chemical Reactions 1 and 2.

(Chemical Reaction 1)

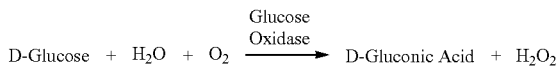

(Chemical Reaction 2)

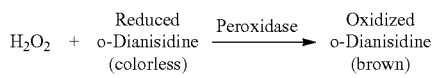

According to the Chemical Reactions 1 and 2 above, the glucose in blood forms hydrogen peroxide ($H_2O_2$) by reacting with glucose oxidase, and O-dianisidine, by reacting with hydrogen peroxide, turns from colorless to brown.

Additionally, in the reagent 130, the weight ratio between at least one selected from: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase may be in the range of from 0.01 to 40, preferably from 0.05 to 5, and more preferably from 0.1 to 2. Here, when the weight ratio is below 0.01 the rate of oxidation of blood glucose becomes decreased, whereas when the weight ratio exceeds 40 the increase rate in the oxidation of glucose will be negligible.

Additionally, the reagent may further contain a peroxidase. The weight ratio of peroxidase relative to glucose oxidase may be in the range of from 0.01 to 10, preferably from 0.05 to 5, and more preferably from 0.1 to 1. Here, when the weight ratio is below 0.01 the rate of oxidation of O-dianisidine becomes decreased, whereas when the weight ratio exceeds 10 the increase rate in the oxidation of O-dianisidine will be negligible.

The reagent 130 may be formed by, for example, dropping it in the reaction region 112 using a pipette followed by drying, but is not limited thereto.

The reagent 130 may further contain a peroxidase. Therefore, peroxidase may be distributed on the reaction region 112 along with the reagent 130. The peroxidase serves as a catalyst to accelerate the Chemical Reaction 2.

On the second substrate 120 is formed an additional aperture 122 apart from the blood aperture 121. The aperture 122 may be formed on a position corresponding to an end of the reaction region 112. When the blood volume entered into the blood inflow region 111 is in excess, part of the blood may pass through the reaction region 112 and be released out via the aperture 122 formed on the second substrate 120.

In an embodiment of the present invention, the blood glucose measurement unit 100 may further include the third substrate 140 to be inserted between the first substrate 110 and the second substrate 120.

The third substrate 140 has a light transmittance. The transparent third substrate 140 may include at least one selected from the group consisting of: polyester, polyacrylate, polyethylene (PE), polyethersulfone (PES), polycarbonate (PC), polyarylate (PAR), polyimide (PI) and glass, but is not limited thereto.

For example, when the third substrate 140 is manufactured using polyester it may have a shape of a thin film such as an overhead projector (OHP) film. The blood glucose measurement unit 100 manufactured as such will have an improved flexibility thus being convenient to transport.

On the third substrate 140 may be formed a blood aperture 141 through which the blood being flowed into the blood inflow region 111 passes. The blood aperture 141 may be formed in a position corresponding to the blood inflow region 111. The blood aperture 141 on the third substrate 140 may be formed in a size smaller than that of the blood aperture 121 on the second substrate 120. In this case, the blood passages formed by the blood apertures 121 and 141 may have a funnel shape enabling an effective transport of blood toward the blood inflow region 111.

On the third substrate 140 may be formed an additional aperture 142 apart from the blood aperture 141. The aperture 142 may be formed in a position corresponding to the aperture 122 of the second substrate 120.

Two different adhesive layers 150 and 160 may be respectively inserted between the first substrate 110 and the third substrate 140, and in between the second substrate 120 and the third substrate 140. The adhesive layers 150 and 160 may be respectively formed using an adhesive film or an adhesive.

Referring to FIG. 2, an aperture 151 may be formed on the adhesive layer 150 inserted between the first substrate 110 and the third substrate 140 not to be interfered with the reaction region 112. Additionally, two apertures 161 and 162 are formed on the adhesive layer 160, which is inserted between the second substrate 120 and the third substrate 140, corresponding to the blood aperture 121 and 141, and apertures 122 and 142, respectively formed on the second substrate 120 and the third substrate 140.

In an embodiment of the present invention, the blood glucose measurement unit 100 may further include a filter 170 disposed between the first substrate 110 and the second substrate 120. The filter 170 filters out proteins and corpuscles contained in the blood that passes through the blood aperture 121. Since the amount of blood cells differs from person to person it is effective to measure the blood glucose level after removing proteins and corpuscles from the blood. This is because the blood glucose level is measured in the present invention by means of measuring the degree of light transmittance relative to the blood glucose measurement unit 100. The method of measuring blood glucose level according to an embodiment of the present invention using the blood glucose measurement unit 100 will be described in detail later.

The filter 170 may contain nitrocellulose, polysulfone and nonwoven fiber, but is not limited thereto. The filter 170 may be manufactured in a thin film shape, and may be disposed to cover up the blood aperture 121.

Referring to FIG. 1, the blood glucose measurement system 1 according to an embodiment of the present invention may include a CMOS image sensor 5. The CMOS image sensor (CIS) 5 is a sensor that detects an optical signal and converts it into a digital electric signal. The CMOS image sensor 5 is easy to operate, can be embodied in various scanning methods, and integrated on a single chip thus enabling the miniaturization of its products. Additionally, the CMOS image sensor 5 can reduce manufacturing cost because of its compatible use of a CMOS processing technology, and its low power consumption enables it to be easily applicable to products with limited battery capacity.

The operating principle of the CMOS image sensor 5 is as follows. There is a photodiode present in the sensor and the photodiode absorbs light and converts into a different signal according to the photoelectric effect. When photons are accumulated in the form of an electric charge and converted from electrons the amount corresponds to the number of photons being detected after their arrival at the CMOS image sensor. The accumulated charges are amplified in the form of an analog voltage and then converted into digital numbers. The numbers displayed on the digital output correspond to the numbers of the photons detected in the image sensor. Therefore, any impurities present on the surface of the sensor would prevent the passage of the photons thereby reducing the degree of digital output.

According to an embodiment of the present invention, visible light may be used as a light source, but is not limited thereto. The CMOS image sensor 5 may be installed on a smart phone (not shown) or a camera (not shown). Due to the recent rapidly growing smart phone penetration rate, the blood glucose level of a person can be promptly and effectively measured using the CMOS image sensor 5 installed in a smart phone. Here, an application enabling a quantitative expression of photon numbers may be installed in a smart phone already equipped with the CMOS image sensor 5. The application as described above can be easily installed in a camera with a built-in CMOS image sensor.

Figure 3:
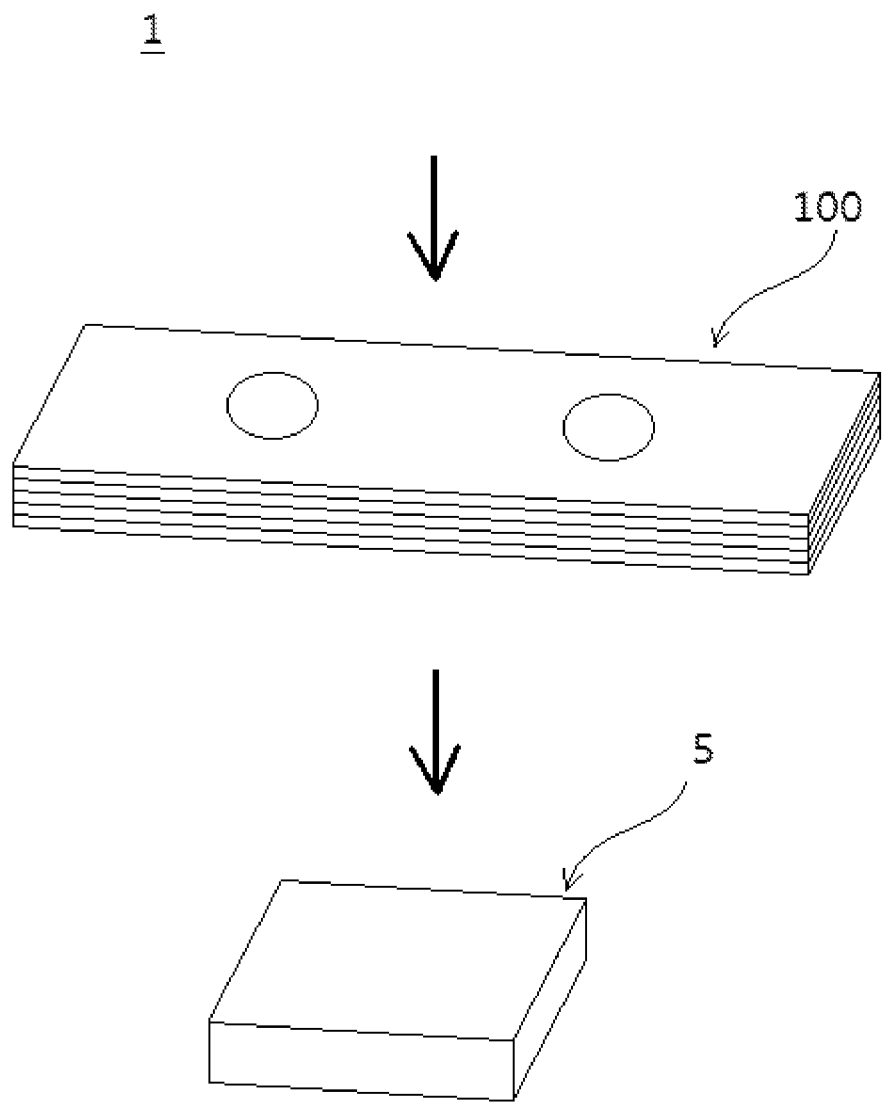
FIG. 3 is a schematic diagram illustrating a method for measuring the blood glucose level according to an embodiment of the present invention.

FIG. 3 is a schematic diagram illustrating a method for measuring a blood glucose level according to an embodiment of the present invention. In FIG. 3, the arrow indicates the direction of light. The blood glucose measurement method according to an embodiment of the present invention will be explained herein below referring to FIG. 3. Nevertheless, the blood glucose measurement method according to the embodiment of the present invention will be explained as being performed by the blood glucose measurement system 1 described above, but is not limited thereto.

The number of photons that penetrate the blood glucose measurement unit 100 is measured using the CMOS image sensor 5 in advance, and the number of photons measured thereof becomes the standard value.

Once a given blood sample is injected into the blood glucose measurement unit 100, the blood reacts with a reagent contained in the blood glucose measurement unit 100. Here, the chemical reactions involved between the blood glucose and the reagent are the same as in Chemical Reactions 1 and 2 shown above. When blood glucose reacts with the reagent the reaction region turns to brown, and becomes darker as the amount of the blood glucose increases.

Then, the number of photons that penetrate the blood glucose measurement unit 100 is measured again using the CMOS image sensor 5. Here, the reaction region of the blood glucose measurement unit 100 turns to brown and interrupts light penetration and thus the number of photons being detected by the CMOS image sensor 5 falls short of the standard number of photons.

Subsequently, the blood glucose level can be calculated by comparing the standard number of photons and the number of photons measured after the reaction.

The results of the experiments conducted in the present invention are schematically explained herein below.

In the experiments, the reagent contained O-dianisidine and glucose oxidase/peroxidase, wherein O-dianisidine and glucose oxidase/peroxidase was mixed therein in a 2:1 weight ratio, and glucose oxidase and peroxidase were mixed therein in a 5:1 weight ratio.

A certain amount of blood glucose was dropped on the blood glucose measurement unit to react with the reagent at room temperature for 3 minutes. Then, the number of photons that penetrate the blood glucose measurement unit was measured using the CMOS image sensor.

Light transmittance is measured based on the current value released from the CMOS image sensor. The maximum current value of light transmittance of a chip on which the reagent was placed thereon was set at 170. Then, blood glucose samples at various concentrations were injected therein and the maximum values were measured. Accordingly, the higher the blood glucose concentration the darker the color of the reaction region, and the maximum current value released from the image sensor will be reduced.

The light transmittance measured according to the blood glucose concentration in the experiments is shown in Table 1 below.

TABLE 1

| Glucose concentration (μg/mL) | Measured Light Transmittance |
| --- | --- |
| 500 | 158 |
| 1000 | 153 |
| 1500 | 148 |
| 2000 | 140 |
| 2500 | 138 |
| 3000 | 136 |
| 3500 | 135 |
| 4000 | 130 |
| 4500 | 126 |
| 5000 | 123 |

Referring to Table 1, it was confirmed that the higher the blood glucose concentration the lower the light transmittance measured therefrom. This is because the reaction region becomes darker with the increase in the blood glucose concentration, and the number of photons that penetrate the reaction region becomes smaller thereby lowering the light transmittance. When the experimental results as such are data-based the blood glucose level of a given blood sample can be measured by measuring its light transmittance after dropping a certain amount of blood on the blood glucose measurement unit.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the present invention enables a real-time effective measurement of blood glucose level using a portable blood glucose measurement unit and a CMOS image sensor. In particular, since the CMOS image sensor can be installed on a smart phone, the portability of the blood glucose measurement unit can be maximized.

The invention claimed is:

1. A blood glucose measurement unit comprising:
    a transparent first substrate comprising a blood inflow region into which blood flows and a reaction region connected to the blood inflow region, wherein the blood inflow region and the reaction region are formed on a surface of the first substrate;
    a transparent second substrate coupled to the first substrate and comprising a blood aperture through which the blood flowing into the blood inflow region passes;
    a transparent third substrate provided between the first substrate and the second substrate, and comprising a blood aperture, through which the blood flowing into the blood inflow region passes;
    a filter provided between the second substrate and the third substrate so as to separate proteins and blood corpuscles out of the blood which passes through the blood aperture; and
    a reagent distributed to the reaction region so as to react with the glucose in the blood which has flown into the blood inflow region,
    wherein the surface of the first substrate is a top surface of the first substrate and the reagent is placed between the top surface of the first substrate and the third substrate.

2. The blood glucose measurement unit of claim 1, wherein the reagent comprises at least one selected from: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase.

3. The blood glucose measurement unit of claim 1, wherein a weight ratio between at least one selected from: O-dianisidine, O-toluidine-Blue, potassium iodide, tetra methyl benzidine, Meta[3-methyl-2-benzothiazolinonehydrazone] (N-sulfonyl benzenesulfonate monosodium combined with 8-anilino-1-naphthalene sulfonic acid ammonium (MBTHSB-ANS), 3,3',5,5'-tetramethylbenzidine and syringaldazine, primaquine diphosphate, thiazole yellow G and Auramine O-anhydrous; and glucose oxidase in the reagent is in the range of from 0.01 to 40.

4. The blood glucose measurement unit of claim 1, wherein the reagent further comprises peroxidase.

5. The blood glucose measurement unit of claim 1, wherein the filter comprises at least one selected from the group consisting of nitrocellulose, polysulfone and nonwoven fiber.

6. The blood glucose measurement unit of claim 1, wherein a projection surrounding the blood inflow region is formed on one surface of the first substrate, and an opening is formed on the projection so that the blood in the blood inflow region can move to the reaction region.

7. The blood glucose measurement unit of claim 1, wherein an aperture is formed on the position of the second substrate, which corresponds to an end of the reaction region.

8. The blood glucose measurement unit of claim 1, wherein the first substrate and the second substrate respectively comprise at least one selected from the group consisting of: polyester, polyacrylate, polyethylene (PE), polyethersulfone (PES), polycarbonate (PC), polyarylate (PAR), polyimide (PI) and glass.

9. A blood glucose measurement system, comprising:
    a blood glucose measurement unit of claim 1; and
    a CMOS image sensor for counting the number of photons that penetrate the blood glucose measurement unit.

10. The blood glucose measurement system of claim 9, wherein the CMOS image sensor is installed on at least one selected from the group consisting of smart phones and cameras.

* * * * *